US007101942B2

(12) United States Patent
Moszner et al.

(10) Patent No.: US 7,101,942 B2
(45) Date of Patent: Sep. 5, 2006

(54) DENTAL MATERIALS BASED ON METAL OXIDE CLUSTERS

(75) Inventors: Norbert Moszner, Eschen (LI); Thomas Völkel, Oberreitnau (DE); Volker Rheinberger, Vaduz (LI); Ulrich Schubert, Wöllersdorf (AT)

(73) Assignee: Ivoclar Vivadent AG, Schaan (LI)

( * ) Notice: Subject to any disclaimer, the term of this patent is extended or adjusted under 35 U.S.C. 154(b) by 503 days.

(21) Appl. No.: 10/053,460

(22) Filed: Jan. 18, 2002

(65) Prior Publication Data

US 2003/0004294 A1    Jan. 2, 2003

Related U.S. Application Data

(60) Provisional application No. 60/306,093, filed on Jul. 17, 2001.

(30) Foreign Application Priority Data

Jan. 19, 2001    (DE)    ............................... 101 02 297

(51) Int. Cl.
C08F 30/04    (2006.01)

(52) U.S. Cl. ...................... 526/240; 526/241; 526/319; 526/321; 528/403; 528/406; 528/395; 523/109; 523/115; 523/116; 523/117

(58) Field of Classification Search .............. 526/240, 526/241; 523/109, 115, 116, 117; 528/395
See application file for complete search history.

(56) References Cited

U.S. PATENT DOCUMENTS

| 5,064,877 A * | 11/1991 | Nass et al. ................... 522/172 |
| 5,508,342 A | 4/1996 | Antonucci et al. |
| 5,589,537 A * | 12/1996 | Golden et al. .............. 524/780 |
| 6,096,903 A | 8/2000 | Moszner et al. |
| 6,492,540 B1 * | 12/2002 | Su et al. ........................ 556/30 |
| 6,555,640 B1 * | 4/2003 | Ito et al. ..................... 526/207 |

FOREIGN PATENT DOCUMENTS

| DE | 31 37 840 C2 | 9/1981 |
| DE | 41 33 494 C2 | 10/1991 |
| DE | 44 16 857 C1 | 5/1994 |
| DE | 196 34 189 A1 | 8/1996 |
| DE | 198 46 660 A1 | 10/1998 |
| EP | 1 022 012 A2 | 7/2000 |
| JP | 03177470 A2 | 8/1991 |
| WO | WO 92/11837 | 7/1992 |
| WO | WO 96/13538 | 5/1996 |
| WO | WO 98/46197 | 10/1998 |
| WO | WO 98/47047 | 10/1998 |
| WO | WO 00/69392 | 11/2000 |

OTHER PUBLICATIONS

Article found at http://www.tdx.cesca.es/TESIS_URV/AVAILABLE/TDX-0426104-095633//capitol1.pdf entitled "Introduction to Polyoxometalates and Scope of the Work".*
Abstract for "Inorganic Clusters in Organic Polymers and the use of Polyfunctional Inorganic Compounds as Polymerization Initiators" Monatshefte fuer Chemie (2201, 132(1), p. 13-30.*
Abstract for "Hybrid Organic-inorganic Copolymers based on Oxohydroxo Organotin Nanobuilding Blocks" Journal of Sol Gel Science and Technology (1997), 8(1/2/3), 529-533.*
"Crosslinking of Poly(methyl methacrylate) by the Methacrylate-Substituted Oxozirconium Cluster $Zr_6(OH)_4(methacrylate)_{12}$" authored by Schubert et al. and published in Chem. Mater. (2000), 12, p. 602-604.*
"Polymers Reinforced by Covalently Bonded Inorganic Cluster" authored by Schubert et al. and published in Chem. Mater. (2001), 13, p. 3487-3494.*
Schubert et al., "Inorganic-Organic Hybrid Polymers from Surface-Modified Oxometallate Clusters," *Mat. Res. Soc. Symp. Proc.*, 628:CC2.3.1-CC2.3.11 (2000).
Schubert et al., "Nanoscale Structures of Sol-Gel Materials," *Mol. Cryst. and Liq. Cryst.*, 34:107-122 (2000).
Yoshida et al., "Effects of Coupling Agents on Mechanical Properties of Metal Oxide-Polymethacrylate Composites," *J. Dent.*, 22(1):57-62 (1994) (abstract only).
Schubert et al., "Primary Hydrolysis Products of Methacrylate-Modified Titanium and Zirconium Alkoxides," *Chem. Mater.*, 4:291-295 (1992).
Kiekelbick et al., "Oxozirconium Methacrylate Clusters: $Zr_6(OH)_4O_4(OMc)_{12}$ and $Zr_4O_2(OMc=Methacrylate)$," *Chem. Ber./Recueil*, 130:473-477 (1997).
Rawls et al., "Radiopaque Acrylic Resins Containing Miscible Heavy-Metal Compounds," *Dent. Mater.*, 6(4):250-255 (1990) (abstract only).
Loebenstein, "Coupling Agents for Improved Bonding of *Dental* Composites," *J. Dent. Res.*, 57(3):480 (1978) (abstract only).
Skrtic et al., "Physicochemical Evaluation of Bioactive Polymeric Composites Based on Hybrid Amorphous Calcium Phosphates," *J. Biomed. Mater. Res.*, 53(4):381-391 (2000) (abstract only).

* cited by examiner

*Primary Examiner*—Marc S. Zimmer
(74) *Attorney, Agent, or Firm*—Nixon Peabody LLP

(57) ABSTRACT

Dental material containing a cluster according to the general formula $[(M^1)_a(M^2)_bO_c(OH)_d(OR)_e(L-Sp-Z)_f]$ (I) in which $M^1$, $M^2$, independently of each other, stand in each case for a metal atom of the IIIrd or Vth main groups or the Ist to VIIIth sub-groups of the periodic table; R is an alkyl group with 1 to 6 carbon atoms; L is a co-ordinating group with 2 to 6 complexing centres; Sp is a spacer group or is absent; Z is a polymerizable group; c is a number from 1 to 30; d, e, independently of each other, are in each case a number from 1 to 30; f is a number from 2 to 30, any charge of the cluster (I) present being equalized by counterions.

11 Claims, No Drawings

DENTAL MATERIALS BASED ON METAL OXIDE CLUSTERS

This application claims the benefit of U.S. Provisional Patent Application No. 60/306,093, filed Jul. 17, 2001, which is herein incorporated by reference in its entirety.

The invention relates to dental materials based on polymerizable metal oxide clusters.

Polymerizable compositions are known which, in addition to organic monomers, also contain polymerizable metal compounds.

U.S. Pat. No. 2,502,411 discloses compositions which, in addition to unsaturated polymerizable organic compounds, contain a zirconium acrylate which is obtainable by reacting a water-soluble zirconium salt with a salt of (meth)acrylic acid. The zirconium compound is said to improve the wettability of ceramics, metals and cellulose. Details of the structure of the zirconium acrylates are not given.

DE 31 37 840 C2 discloses crystalline zirconium methacrylate of the general formula $Zr_4(MAS)_{10}O_2X_2(H_2O)_{2-4}$ in which MAS is the anion of methacrylic acid and X an anion from the group hydroxide, alkoxide, halide and carboxylate. The compounds are said to be suitable as cross-linking agents in the preparation of vinyl polymers by radical polymerization of vinyl monomers.

Schubert et al., Chem. Mater 4 (1992) 291 describe the preparation and characterization of methacrylate-modified titanium and zirconium alkoxides which are obtainable by reaction of the corresponding metal alcoholates with methacrylic acid, and Kickelbick and Schubert, Chem. Ber./ Recueil 130 (1997) 473, of crystalline oxozirconium methacrylate clusters of the formulae $Zr_6(OH)_4O_4(OMc)_{12}$ and $Zr_4O_2(OMc)_{12}$ in which OMc is the anion of methacrylic acid.

DE 41 33 494 C2 discloses dental resin compositions based on polymerizable polysiloxanes which are prepared by hydrolytic condensation of one or more silanes of which at least one is substituted by a 1,4,6-trioxaspiro-[4,4]-nonane radical or an ethylenically unsaturated group.

Hydrolyzable and polymerizable silanes are known from DE 44 16 857 C1 which contain one linear or branched organic radical with at least one C=C double bond and 4 to 50 carbon atoms.

EP 1 022 012 A2 and U.S. Pat. No. 6,096,903 disclose dental materials based on polymerizable and hydrolyzable methacrylate-modified or oxetane-group-containing silanes.

Silanes of the type described above can be condensed alone or together with another hydrolytically condensable compounds to form inorganic networks, which can then be cured via the C=C double bonds contained in the silanes by ionic or radical polymerization accompanied by the formation of inorganic-organic networks.

The object of the invention is to provide dental materials with improved mechanical properties.

This object is achieved by dental materials which contain at least one cluster according to the general formula (I)

$$[(M^1)_a(M^2)_bO_c(OH)_d(OR)_e(L\text{-}Sp\text{-}Z)_f] \quad (I)$$

in which

| | |
|---|---|
| $M^1, M^2$ | independently of each other, stand for a metal atom of the IIIrd or Vth main groups or the Ist to VIIIth sub-groups of the periodic table; |
| R | is an alkyl group with 1 to 6 carbon atoms; |
| L | is a coordinating group with 2 to 6 complexing centres; |
| Sp | is a spacer group or is absent; |
| Z | is a polymerizable group; |
| a | is a number from 1 to 20; |
| b | is a number from 0 to 10; |
| c | is a number from 1 to 30; |
| d, e | independently of each other, are in each case a number from 0 to 30; |
| f | is a number from 2 to 30. |

The respective values of the indices a to f can vary according to the type, number and valency of the metals and ligands. The indices c, d, e and f preferably assume such values that the positive charges of the metals $M^1$ and $M^2$ are completely equalized and the cluster is neutral. The cluster can however also be positively or negatively charged. In this case, the charge of the cluster is compensated by suitable counterions such as for example $H^+$, alkali or alkaline-earth metal ions, $NH_4^+$, $NR^\theta{}_4^+$ with $R^\theta$=alkyl, in particular $C_1$ to $C_4$ alkyl, or $OH^-$, $R'$—$COO^-$ with $R'$=alkyl, preferably $C_1$ to $C_{10}$ alkyl, particularly preferably $C_1$ to $C_4$ alkyl, or halide, preferably $F^-$ or $Cl^{31}$. The clusters (I) have for example a charge of −4 to +4, in particular +1 to +4.

The group L can be chelating or bridging, i.e. the complexing centres of the group L can be connected to the same metal atom or preferably with two or more different metal atoms.

The ligand (L-Sp-Z) can be neutral or have a negative charge. Neutral ligands or ligands with a single to triple negative charge are preferred.

The ligands (L-Sp-Z) present in the cluster can be the same or different. Clusters which contain 1 to 4, preferably 1 or 2 kinds of ligands (L-Sp-Z) are preferred. For example, two methacrylate ligands can be replaced by allyl acetoacetate in the cluster $Zr_4O_2$(methacrylate)$_{12}$. The resulting cluster has the formula $Zr_4O_2$(methacrylate)$_{12}$(allyl acetoacetate)$_2$, both methacrylate and allyl acetoacetate being ligands of the type (L-Sp-Z), i.e. the cluster contains two kinds of ligands of the type (L-Sp-Z).

Clusters which contain only a small proportion of alkoxy groups (d>e) are preferred. Preferably $e \leq (a+b)$, particularly preferably e=0.

Preferred definitions, which can be selected independently of each other, for the individual variables are:

| | |
|---|---|
| $M^1, M^2 =$ | independently of each other, Ti and/or Zr; |
| R = | an alkyl group with 1 to 4 carbon atoms, in particular 1 to 2 carbon atoms; |
| L = | α-hydroxycarboxylate (—CH(OH)—COO$^-$), α-aminocarboxylate (—CH(NH$_2$)—COO$^-$), β-diketonate ([—C(—O$^-$)=CH—C(=O)R$^K$]; with $R^K$ = alkyl, preferably $C_1$ to $C_6$ alkyl, particularly preferably $C_1$ to $C_3$ alkyl, in particular methyl, sulfonate (—SO$_3^-$) or phosphonate (—PO$_3^{2-}$), particularly preferably carboxylate (—COO$^-$); |
| Sp = | an alkylene group with 1 to 18 carbon atoms, an oxyalkylene group with 1 to 18 carbon atoms and 0 to 6 oxygen atoms or an arylene group with 6 to 14 carbon atoms, the spacer Sp being able to contain one or more, preferably 0 to 2 of the groups O, S, CO—O, O—CO, CO—NH, NH—CO, O—CO—NH, NH—CO—O and NH; particularly preferably, Sp is an alkylene group with 1 to 6, in particular 1 to 3 carbon atoms or is absent; |

-continued

| | |
|---|---|
| Z = | an ethylenically unsaturated group, an epoxide, oxetane, vinyl ether, 1,3-dioxolane, spiroorthoester, particularly preferably a methacrylic and/or acrylic group; |
| a = | 2 to 11; |
| b = | 0 to 4. |

The values of the indices c, d, e and f again correlate to the number and charge of the metal atoms. Preferably, they assume values such that the charge of the cluster is equalized. Typical values for c are in the case c)f the preferred clusters 1 to 11, in particular 2 to 5, for d and e 0 to 10 and in particular 0 to 8, for f 4 to 20 and in particular 6 to 15.

According to a particularly preferred version, $M^1=M^2$. Clusters in which $M^1$ and $M^2$ are each zirconium are particularly preferred.

The polymerizable groups Z are preferably bound to the metal centres direct or by a short spacer via carboxylate groups.

Particularly preferred ligands of the type (L-Sp-Z) are acrylate, methacrylate, oleate, allyl acetoacetate and acetoacetoxyethyl methacrylate.

Particularly preferred clusters are:
$Zr_6(OH)_4O_4(OMc)_{12}$; $Zr_4O_2(OMc)_{12}$; $Zr_6O_2(OC_4H_9)_{10}(OMc)_{10}$; $Ti_6O_4(OC_2H_5)_8(OMc)_8$; $Ti_4O_2(O-i-C_3H_7)_6(OMc)_6$; $Ti_4O_2(O-i-C_3H_7)_6(OMc)_6$; $Ti_9O_8(OC_3H_7)_4(OMc)_{16}$; $Zr_4Ti_2O_4(OC_4H_9)_2(OMc)_{14}$; $Zr_2Ti_4O_4(OC_4H_9)_6(OMc)_{10}$; $Zr_4Ti_4O_6(OBu)_4(OMc)_{16}$; and $Zr_6Ti_2O_6(OMc)_{20}$, OMc in each case standing for a methacrylate group. Similarly preferred are the clusters which contain acrylate groups instead of the methacrylate groups.

The clusters according to formula (I) can be prepared by reacting metal alkoxides with suitable polymerizable ligands, optionally with the addition of water. For example, the reaction of zirconium(IV)-propoxide $(Zr(O-C_3H_7)_4)$ with a quadruple molar excess of methacrylic acid (HOMc) produces clusters of the composition $Zr_4O_2(OMc)_{12}$ (G. Kickelbick, U. Schubert, Chem. Ber./Recueil 130 (1997) 473):

$$4Zr(OC_3H_7)_4 + 14HOMc \rightarrow Zr_4O_2(OMc)_{12} + 2C_3H_7OMc + 14C_3H_7OH$$

Moreover, suitable clusters can be prepared by the exchange of ligands for polymerizable ligands. For example, the reaction of titanium oxide clusters $Ti_aO_c(OOCR^\alpha)_e$ with unsaturated carboxylic acids $(HOOCR^\beta)$ produces clusters of the composition $Ti_aO_c(OOCR^\alpha)_{e-u}(OOCR_\beta)_u$. Specifically, the reaction of the titanium carboxylate cluster $Ti_6O_4(OC_2H_5)_8(acetate)_8$ with methacrylic acid (HOMc) produces the cluster 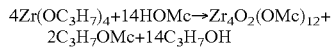.

Alternatively, suitable clusters can be obtained by the derivatization of inorganic clusters. For example, the reaction of $SiW_{11}O_{39}^{8-}$ with trichloro- or triethoxysilanes $R_7SiQ_3$ (Q=Cl or $OC_2H_5$) in which $R^{65}$ contains a polymerizable group produces polymerizable clusters of the composition $SiW_{11}O_{39}(OSi_2R_2)^{4-}$.

The clusters according to formula (I) represent substances of high reactivity which can be processed alone or preferably in combination with other polymerizable components by polymerization to form mechanically stable layers, moulded bodies and fillers. These are characterized by a very small proportion of monomers which can be dissolved out by solvents and a high stability even in humid conditions. The mechanical properties of the cured materials are not impaired by water storage.

For curing, an initiator for ionic or radical polymerization is preferably added to the polymerizable clusters or mixtures of the clusters with other polymerizable components. Depending on the type of initiator used, the polymerization can be initiated thermally, by UV or visible light. In addition, the mixtures can contain further additives, such as for example colorants (pigments or dyes), stabilizers, flavoring agents, microbicidal active ingredients, plasticizers and/or UV absorbers. The clusters according to formula (I) and their mixtures are suitable in particular for use as dental materials or for the preparation of dental materials. By dental materials are preferably meant adhesives, coating materials, cements and in particular filling materials.

The clusters according to formula (I) have only a low volatility because of their high molecular weight and can therefore largely be safely processed. Through the size and structure as well as the number of polymerizable groups of the clusters, the cross-linking density and thereby the mechanical properties such as E-modulus and strength and the swelling behaviour in organic solvents of the cured materials can be selectively set. Size and structure of the clusters as well as the number of polymerizable groups per metal atom can be monitored by variations in the synthesis parameters. The cluster size and structure are governed by the ratio of metal oxide to ligand in the educt mixture, but also by the nature of the radicals R in the alkoxides $M^1(OR)_n$ or $M^2(OR)_n$ used. Furthermore, the mechanical properties such as strength and flexibility can be influenced via the distance between the metal centres and polymerizable radicals, i.e. via the length of the spacer groups -Sp-.

In the case of the clusters according to formula (I), the polymerizable groups are fixed to a compact particulate cluster structure. The result of this is that, upon polymerization, rigid products with a high cross-linking density are obtained. The clusters represent three-dimensional molecules with a defined spatial structure and size and allow, upon co-polymerization with other components, an optimum cross-linking density to be set for the purpose in question. The structure of the clusters guarantees a complete incorporation of the clusters into the polymer network. It ensures a uniform environment for all the polymerizable organic ligands, so that these are practically equivalent as regards their reaction with organic co-monomers, which results in a uniform polymer structure developing around each ligand.

In addition, the abrasiveness or the optical properties such as for example the refractive index can be varied via the type and number of metal atoms.

Substances in which the clusters are soluble, i.e. liquid materials in particular, are preferred as further polymerizable components. Radically or ionically polymerizable mono- and polyfunctional compounds can primarily be considered here, in particular polymerizable organic monomers and silanes and polysiloxanes with polymerizable groups as well as mixtures of these compounds.

Ethylenically unsaturated organic monomers, in particular monofunctional or polyfunctional methacrylates which can be used alone or in mixtures are preferred as polymerizable organic monomers. Mono(meth)acrylates such as methyl, ethyl, butyl, benzyl, furfuryl, phenyl(meth)acrylate, isobutyl (meth)acrylate, cyclohexyl(meth)acrylate and polyfunctional (meth)acrylates such as tetraethylene glycol di(meth) acrylate, urlethylene glycol di(meth)acrylate, diethylene glycol di(meth)acrylate, ethylene glycol di(meth)acrylate, polyethylene glycol di(meth)acrylate, butanediol di(meth)

acrylate, hexanediol di(meth)acrylate, 1,10-decanediol di(meth)acrylate, 1,12-dodecanediol di(meth)acrylate, bisphenol-A di(meth)acrylate, trimethylolpropane tri(meth) acrylate, 2,2-bis-4-(3-methacryloxy-2-hydroxypropoxy)-phenylpropane (bis-GMA), pentaerythritol tetra(meth)acrylate as well as the reaction products from isocyanates, in particular di- and/or triisocyanates, and OH-group-containing (meth)acrylates can be considered as preferred examples of these compounds. Examples of these are the reaction products of 1 mol 2,2,4-trimethylhexamethylene diisocyanate with 2 mol 2-hydroxyethylene methacrylate (UDMA) or 2 mol hydroxypropyl methacrylate as well as the reaction products of 2 mol glycerin dimethacrylate with 1 mol 2,2,4-trimethylhexamethylene diisocyanate, isophoron diisocyanate or α,α,α',α'-tetramethyl-xylylene-m-diisocyanate. The use of polyfunctional (meth)acrylates is particularly preferred. By polyfunctional compounds are meant those with several polymerizable groups.

Further preferred polymerizable organic monomers are cationically polymerizable mono- or polyfunctional monomers such as 3,4-epoxycyclohexylmethyl-3,4-epoxycyclohexane carboxylate, bis-(3,4-epoxycyclohexylmethyl)adipate, vinylcyclohexene dioxide, 3-ethyl-3-hydroxymethyl oxetane, 1,10-decanediylbis(oxymethylene)bis(3-ethyloxetane) and 3,3-(4-xylylenedioxy)-bis-(methyl-3-ethyl-oxetane).

Compounds which have polymerizable groups, preferably (meth)acryl groups, or cationally polymerizable groups, preferably epoxide, oxetane, spiroorthoesters or vinyl ether groups, are particularly suitable as polymerizable silanes and polysiloxanes. Suitable silanes and polysiloxanes and their preparation are described in DE 41 33 494 C2, DE 44 16 857 C1, EP 1 022 012 A2 and U.S. Pat. No. 6,096,903. Preferred silanes are listed below. Polysiloxanes based on these silanes are particularly preferred, the polysiloxanes being able to be present in the form of the homo- and co-condensates.

Silanes of the general formula (1) are preferred $$Y^1{}_{n1}SiX^1{}_{m1}R^1{}_{4-(n1+m1)} \quad (1)$$

in which the radicals $X^1$, $Y^1$ and $R^1$ are the same or different and have the following meanings:

| | |
|---|---|
| $R^1 =$ | alkyl, alkenyl, aryl, alkylaryl or arylalkyl, |
| $X^1 =$ | hydrogen, halogen, hydroxy, alkoxy, acyloxy, alkylcarbonyl, alkoxycarbonyl or $NR^\delta{}_2$ with $R^\delta =$ hydrogen, alkyl or aryl, |
| $Y^1 =$ | a substituent which contains a substituted or unsubstituted 1,4,6-trioxaspiro-[4,4]-nonane radical, |
| $n^1 =$ | 1, 2 or 3, |
| $m^1 =$ | 1, 2 or 3, with $n^1 + m^1 \leq 4$, | and silanes of the general formula (2), $$\{X^1{}_{n1}R^1{}_{k1}Si[R^2(A^1)_l]_{4-(n1+k1)}\}_{x1}B^1 \quad (2)$$

in which radicals $A^1$, $R^1$, $R^2$ and $X^1$ are the same or different and have the following meanings:

| | |
|---|---|
| $A^1 =$ | O, S, $PR^\varepsilon$, $POR^\varepsilon$, NHC(O)O or NHC(O)ONR$^\varepsilon$, with $R^\varepsilon$ = hydrogen, alkyl or aryl, |
| $B^1 =$ | a linear or branched organic radical which is derived from a compound $B^{1'}$ with at least one (for $l = 1$ and A = NHC(O)O or NHC(O)NR$^\zeta$) or at least two C=C double bonds and 5 to 50 carbon atoms, with $R^\zeta$ = hydrogen, alkyl or aryl, |
| $R^1 =$ | alkyl, alkenyl, aryl, alkylaryl or arylalkyl, |
| $R^2 =$ | alkylene, arylene or alkylene arylene, |
| $X^1 =$ | hydrogen, halogen, hydroxy, alkoxy, acyloxy, alkylcarbonyl, alkoxycarbonyl or $NR^\delta{}_2$ with $R^\delta$ = hydrogen, alkyl or aryl, |
| $n^1 =$ | 1, 2 or 3, |
| $k^1 =$ | 0, 1 or 2, |
| $l =$ | 0 or 1, |
| $x^1 =$ | an integer the maximum value of which corresponds to the number of double bonds in the compound $B^1$ minus 1 or is equal to the number of double bonds in the compound $B^1$ when $l = 1$ and A stands for NHC(O)O or NHC(O)ONR$^\varepsilon$. |

The silanes of the general formula (1) and (2) are hydrolyzable and polymerizable, the radicals $X^1$ being hydrolyzable and the radicals $B^1$ and $Y^1$ being polymerizable and in each case at least one radical $B^1$, $X^1$ and $Y^1$ with the above-named meaning being present in the silanes of the general formula (1) and (2). Polysiloxanes based on silanes (1) and/or (2) are preferred polymerizable components.

The alkyl radicals of the compounds (1) and (2) are e.g. linear, branched or cyclic radicals with 1 to 20, preferably 1 to 10 carbon atoms, and lower alkyl radicals with 1 to 6 carbon atoms are particularly preferred. Special examples are methyl, ethyl, N-propyl, i-propyl, n-butyl, s-butyl, t-butyl, i-butyl, n-pentyl, n-hexyl, cyclohexyl, 2-ethylhexyl, dodecyl and octadecyl.

The alkenyl radicals are e.g. linear, branched or cyclical radicals with 2 to 20, preferably 2 to 10 carbon atoms and lower alkenyl radicals with 2 to 6 carbon atoms such as e.g. vinyl, allyl or 2-butenyl are particularly preferred.

Preferred aryl radicals are phenyl, biphenyl and naphthyl.

The alkoxy, acyloxy, alkylcarbonyl, alkoxycarbonyl and amino radicals are preferably derived from the above-named alkyl and aryl radicals. Special examples are methoxy, ethoxy, n- and i-propoxy, n-, i-, s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The radicals named can optionally have one or more substituents, e.g. halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxy, mercapto, cyano, isocyanato, nitro, epoxy, $SO_3H$ and $PO_4H_2$.

Of the halogens, fluorine, chlorine and bromine are preferred.

The substituted or unsubstituted 1,4,6-trioxaspiro[4,4]-nonane groups are bound to the Si atom via alkylene or via alkenylene radicals which can be interrupted by ether or ester groups.

Further preferred are silanes according to the general formula (3) as well as polysiloxanes based on same $$B^2\{A^2-Z^1)_{dl}-R^3-R^5-\underset{\underset{R^4}{|}}{SiX^2{}_{al}R^6{}_{bl}}\}_{cl} \quad (3)$$

in which the radicals and indices have the following meanings:

| | |
|---|---|
| $B^2 =$ | a linear or branched organic radical with at least one C=C double bond and 4 to 50 carbon atoms; |
| $X^2 =$ | hydrogen, halogen, hydroxy, alkoxy, acyloxy, alkylcarbonyl, alkoxycarbonyl or $NR^7_2$; |
| $R^6 =$ | alkyl, alkenyl, aryl, alkylaryl or arylalkyl; |
| $R^5 =$ | alkylene, arylene, arylenealkylene or alkylenearylene with in each case 0 to 10 carbon atoms, these radicals being able to be interrupted by oxygen and sulphur atoms or by amino groups; |
| $R^7 =$ | hydrogen, alkyl or aryl; |
| $A^2 =$ | O, S or NH for $d^1 = 1$ and $Z^1 = CO$ and $R^3 =$ alkylene, arylene or alkylenearylene with in each case 1 to 10 carbon atoms, these radicals being able to be interrupted by oxygen and sulphur atoms or by amino groups, and $R^4 =$ COOH; or |
| $A^2 =$ | O, S or NH for $d^1 = 1$ and $Z^1 = CO$ and $R^3 =$ alkylene, arylene or alkylenearylene with in each case 1 to 10 carbon atoms, these radicals being able to be interrupted by oxygen and sulphur atoms or by amino groups, and $R^4 = H$; or |
| $A^2 =$ | O, S, NH or COO for $d^1 = 1$ and $Z^1 = CHR^n$, with $R^n$ equal to H, alkyl, aryl or alkylaryl, and $R^3 =$ alkylene, arylene or alkylenearylene with in each case 1 to 10 carbon atoms, these radicals being able to be interrupted by oxygen and sulphur atoms or by amino groups, and $R^4 = OH$; or |
| $A^2 =$ | O, S, NH or COO for $d^1 = O$ and $R^3 =$ alkylene, arylene or alkylenearylene with in each case 1 to 10 carbon atoms, these radicals being able to be interrupted by oxygen and sulphur atoms or by amino groups, and $R^4 = OH$; or |
| $A^2 =$ | S for $d^1 = 1$ and $Z^2 = CO$ and $R^3 = N$ and $R^4 = H$; |
| $a^1 =$ | 1, 2 or 3; |
| $b^1 =$ | 0, 1 or 2; |
| $a^1 + b^1 =$ | 3; |
| $c^1 =$ | 1, 2, 3 or 4. |

The silanes of the formula (3) are polymerizable via the radicals $B^2$ and hydrolyzable via the radicals $X^2$.

The optionally present alkcyl, alkenyl, aryl, alkoxy, acyloxy, alkylcarbonyl, alkoxycarbonyl and amino radicals have the meanings defined for the formulae (1) and (2).

For $a^1 \geq 2$ or $b^1 = 2$, the radicals $X^2$ and $R^7$ can in each case have the same or a different meaning. The radical $B^2$ is derived from a substituted or unsubstituted compound $B^2(A^2H)_{c1}$ with at least one C=C double bond, such as e.g. vinyl, alkyl, acryl and/or methacryl groups and 4 to 50, preferably 6 to 30 carbon atoms. Preferably, $B^2$ is derived from a substituted or unsubstituted compound with two or more acrylate or methacrylate groups. Such compounds are also called (meth)acrylates. If the compound $B^2(A^2H)_{c1}$ is substituted, the substituents can be selected from the substituents named above. The group —$A^2$H can be —OH, —SH, —NH$_2$ or —COOH and c can assume values from 1 to 4.

Silanes according to formula (4) and polysiloxanes based on them are particularly preferred

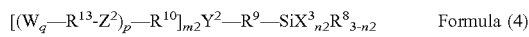   Formula (4)

in which

| | |
|---|---|
| $X^3$ | stands for a halogen atom, a hydroxyl, alkoxy and/or acyloxy group; |
| $n^2$ | is equal to 1 to 3; |
| $R^8$ | stands for an alkyl, alkenyl, aryl, alkylaryl, arylalkyl group; |
| $R^9$ | stands for an alkylene group; |
| $R^{10}$ | stands for a p-times substituted, linear, branched or cyclic, saturated or unsaturated, aromatic or aliphatic organic radical with 2 to 40 carbon atoms and optionally 1 to 6 heteroatoms; |
| $R^{13}$ | stands for a q-times substituted linear, branched or cyclic organic radical with 1 to 20 carbon atoms or is absent; |
| p | is equal to 1 or 2; |
| q | is equal to 1 to 6; |
| $Y^2$ | stands for —$NR^{11}$—, N or —(C=O)—NH—; |
| $m^2$ | is equal to 2 for $Y^2 = N$ and equal to 1 for Y = —$NR^{11}$— or —(C=O)—NH—; |
| $R^{11}$ | stands for an alkyl or aryl group; |
| $Z^2$ | stands for O, S, —(C=O)—O—, —(C=O)—NH—, —O—(C=O)—NH— or is absent; |
| W | stands for $CH_2=CR^{12}$—(C=O)—O—; and |
| $R^{12}$ | stands for a hydrogen atom or an alkyl group. |

Suitable heteroatoms are phosphorus and preferably oxygen.

In connection with formula (4), by alkyl, acyloxy, alkoxy, alkenyl groups and alkylene groups are meant radicals which preferably contain 1 to 25 carbon atoms, particularly preferably 1 to 10 carbon atoms and quite particularly preferably 1 to 4 carbon atoms and optionally bear one or more substitutes such as for example halogen atoms, nitro groups or alkyloxy radicals. By aryl is meant radicals, groups or substituents which preferably have 6 to 10 carbon atoms and can be substituted as stated above. The above definitions also apply to composite groups such as for example alkylary and arylalkyl groups. An alkylaryl group thus designates for example an aryl group as defined above which is substituted with an alkyl group as defined above.

The alkyl, acyloxy, alkoxy, alksenyl groups and alkylene groups can be linear, branched or cyclical.

Preferred definitions, which can be selected independently of each other, for the individual variables of formula (4) are:

| | |
|---|---|
| $X^3 =$ | a methoxy and/or ethoxy group; |
| $n^2 =$ | 2 or 3; |
| $R^8 =$ | a $C_1$ to $C_3$ alkyl group, in particular a methyl group; |
| $R^9 =$ | a $C_1$ to $C_4$ alkylene group; |
| $R^{10} =$ | a p-times substituted linear, branched or cyclic, saturated or unsaturated, aromatic or aliphatic organic radical with 2 to 10 carbon atoms and optionally a hetero atom, preferably an oxygen atom, particularly preferably a $C_1$ to $C_4$ alkenylene radical or a monocyclic radical with 4 to 10, in particular 5 to 8 carbon atoms; |
| $R^{13} =$ | a q-times substituted linear, branched or cyclical organic radical with 1 to 4 carbon atoms, particularly preferably a $C_1$ to $C_3$ alkylene radical; |
| p = | 1 or 2, in particular 1; |
| q = | 1 or 2; |
| $Y^2 =$ | N or —(C=O)—NH—; |
| $Z^2 =$ | —(C=O)—; and/or |
| $R^{12} =$ | a hydrogen atom or a methyl group. |

Hydrolyzable and polymerizable oxetane silanes according to the general formula (5) and their stereoisomers as well as polysiloxanes based thereon are further preferred:

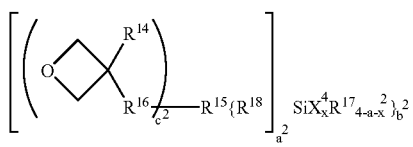

(5)

the variables $R^{14}$, $R^{15}$, $R^{16}$, $R^{17}$, $R^{18}$, $R^{19}$, $R^{20}$, $X^4$, $Y^3$, $a^2$, $b^2$, $c^2$, and $x^2$, unless otherwise stated, having the following meanings independently of each other:

| | |
|---|---|
| $R^{14}$ = | hydrogen or substituted or unsubstituted $C_1$ to $C_{10}$ alkyl; |
| $R^{15}$ = | absent or substituted or unsubstituted $C_1$ to $C_{18}$ alkylene, $C_6$ to $C_{18}$ arylene, $C_7$ to $C_{18}$ alkylenearylene or arylenealkylene, these radicals being able to be interrupted by at least one group selected from ether, thioether, ester, carbonyl, amide and urethane group; |
| $R^{16}$ = | absent or substituted or unsubstituted $C_1$ to $C_{18}$ alkylene, $C_6$ to $C_{18}$ arylene, $C_7$ to $C_{18}$ alkylenearylene or $C_7$ to $C_{18}$ arylenealkylene, these radicals being able to be interrupted by at least one group selected from ether, thioether, ester, thioester, carbonyl, amide and urethane group or bear these in terminal position; |
| $R^{17}$ = | absent or substituted or unsubstituted $C_1$ to $C_{18}$ alkyl, $C_2$ to $C_{18}$ alkenyl, $C_6$ to $C_{18}$ aryl, $C_7$ to $C_{18}$ alkylaryl or $C_7$ to $C_{18}$ arylalkyl, these radicals being able to be interrupted by at least one group selected from ether, thioether, ester, carbonyl, amide and urethane group; |
| $R^{18}$ = | absent or substituted or unsubstituted —$CHR^{20}$—$CHR^{20}$—, —$CHR^{20}$—$CHR^{20}$—S—$R^{19}$—, —S—$R^{19}$—, —$Y^3$—CO—NH—$R^{19}$— or —CO—O—$R^{19}$—; |
| $R^{19}$ = | substituted or unsubstituted $C_1$ to $C_{18}$ alkylene, $C_6$ to $C_{18}$ arylene, $C_6$ to $C_{18}$ alkylenearylene or $C_6$ to $C_{18}$ arylenealkylene, these radicals being able to be interrupted by at least one group selected from ether, thioether, ester, carbonyl, amide and urethane group; |
| $R^{20}$ = | hydrogen or substituted or unsubstituted $C_1$ to $C_{18}$ alkyl or $C_6$ to $C_{10}$ aryl; |
| $X^4$ = | a hydrolyzable group, namely halogen, hydroxy, alkoxy or acyloxy; |
| $Y^3$ = | O or S; |
| $a^2$ = | 1, 2 or 3; |
| $b^2$ = | 1, 2 or 3; |
| $c^2$ = | 1 to 6; and |
| $x^2$ = | 1, 2 or 3; |
| and on condition that (i) $a^2 + x^2 = 2$, 3 or 4 and (ii) $a^2$ and/or $b^2 = 1$. | |

However, the above formulae cover only such compounds which are compatible with the doctrine of valence.

Normally, the silanes according to formula (5) are present as stereoisomer mixtures and in particular as racemic compounds.

The ether, thioether, ester, thioester, carbonyl, amide and urethane groups possibly present in the case of the radicals of formula (5) are defined by the following formulae: —O—, —S—, —CO—O—, —O—CO—, —CO—S—, —S—CO—, —CS—O—, —O—CS—, —CO—, —CO—NH—, —NH—CO—, —O—CO—NH— and —NH—CO—O—.

The non-aromatic radicals or non-aromatic parts of the radicals which can be present in formula (5) can be linear, branched or cyclic.

In the silanes according to formula (5), any alkyl radicals present have preferably 1 to 8 and particularly preferably 1 to 4 carbon atoms. Special examples of possible alkyl radicals are methyl, ethyl, n- and iso-propyl, sec.- and tert.-butyl, n-pentyl, cyclohexyl, 2-ethylhexyl and octadecyl.

In the silanes according to formula (5), any alkenyl radicals present have preferably 2 to 10 and particularly preferably 2 to 6 carbon atoms. Special examples of possible alkenyl radicals are vinyl, allyl- and iso-butenyl.

Preferred examples of possible aryl radicals of the formula (5) are phenyl, biphenyl and naphthyl. Alkoxy radicals have preferably 1 to 6 carbon atoms. Special examples of possible alkoxy radicals are methoxy, ethoxy, n-propoxy, iso-propoxy and tert.-butoxy. Acyloxy radicals have preferably 2 to 5 carbon atoms. Special examples are acetyloxy and propionyloxy.

Preferred alkylene radicals of formula (5) are derived from the above preferred alkyl radicals, and preferred arylene radicals are derived from the above preferred aryl radicals. Preferred radicals which consist of a combination of a non-aromatic and aromatic part are derived from the above preferred alkyl and aryl radicals. Special examples of this are benzyl, 2-phenylethyl and tolyl.

The named substituted R radicals of formula (5) bear one or more single substituents. Examples of these substituents are methyl, ethyl, phenyl, benzyl, hydroxymethyl, hydroxyethyl, methoxy, ethoxy, chlorine, bromine, hydroxy, mercapto, isocyanato, vinyloxy, acryloxy, methacryloxy, allyl, styryl, epoxy, carboxyl, $SO_3H$, $PO_3H_2$ or $PO_4H_2$.

For $a^2$, $b^2$, $c^2$ or $x^2 \geq 2$, the radicals $X^4$ as well as the individual R radicals can in each case have the same or a different meaning.

In addition, preferred definitions exist for the variables of formula (5) set out above which, unless otherwise stated, can be selected independently of each other and are as follows:

| | |
|---|---|
| $R^{14}$ = | hydrogen or $C_1$ to $C_5$ alkyl; |
| $R^{15}$ = | $C_1$ to $C_8$ alkylene, these radicals being able to be interrupted by at least one group selected from ether, thioether, ester and urethane group; |
| $R^{16}$ = | absent or $C_1$ to $C_8$ alkylene, these radicals being able to be interrupted by at least one group selected from ether, thioether, ester, thioester, carbonyl, amide and urethane group or bear these in terminal position; |
| $R^{17}$ = | absent or methyl, ethyl or phenyl; |
| $R^{18}$ = | absent or —$CHR^{20}$—$CHR^{20}$—, —S—$R^{19}$—, —Y—CO—NH—$R^{19}$— or —CO—O—$R^{19}$—; |
| $R^{19}$ = | $C_1$ to $C_8$ alkylene, these radicals being able to be interrupted by at least one group selected from ether, thioether, ester, carbonyl, amide and urethane group; |
| $R^{20}$ = | hydrogen or $C_1$ to $C_5$ alkyl; |
| $X^4$ = | methoxy, ethoxy or chlorine; |
| $Y^3$ = | O or S; |
| $a^2$ = | 1; |
| $b^2$ = | 1; |
| $c^2$ = | 1 to 6; |
| $x^2$ = | 2 or 3; and/or |
| $a^2 + x^2$ = | 3. |

The individual R radicals can in turn bear single substituents.

Preferred compounds according to formula (5) are accordingly those for which at least one of the variables of formula (5) meets the preferred definition described above.

Furthermore, oxetane silanes of formula (5) are preferred for which the indices $a^2$, $b^2$ and/or $c^2$ have the value 1.

The silanes (5) are polymerizable via the oxetane groups and hydrolyzable via the radicals $X^4$.

The above-named silanes can be processed, either alone or together with other hydrolytically condensable compounds of silicon, aluminium, zirconium, titanium, boron, tin, vanadium and/or phosphorus to form polysiloxanes. These additional compounds can be used either per se or already in pre-condensed form.

Preferred further hydrolytically compounds of silicon are silanes of the general formula (6)

$$R^{21}_{k2}(Z^3R^{22})_{m3}SiX^5_{4-(k2+m3)} \qquad \text{Formula (6)}$$

in which

| | |
|---|---|
| $R^{21}$ | stands for a $C_1$ to $C_8$ alkyl, $C_2$ to $C_{12}$ alkenyl or $C_6$ to $C_{14}$ aryl group; |
| $R^{22}$ | stands for a $C_1$ to $C_8$ alkylene, $C_2$ to $C_{12}$ alkenylene or $C_6$ to $C_{14}$ arylene group; |
| $X^5$ | stands for a hydrogen or halogen atom or a $C_1$ to $C_8$ alkoxy group; |
| $Z^3$ | stands for a glycidyl, acryl, methacryl, vinyl, allyl or vinylether group; |
| $k^2$ | is equal to 0, 1, 2 or 3; |
| $m^3$ | is equal to 0, 1, 2 or 3; and |
| $k^2 + m^3$ | is equal to 0, 1, 2 or 3. |

Preferred definitions, which can be selected independently of each other, for the individual variables are:

| | | |
|---|---|---|
| $R^{21}$ | = | a $C_1$ to $C_3$ alkyl, $C_2$ to $C_5$ alkenyl or a phenyl group; |
| $R^{22}$ | = | a $C_1$ to $C_5$ alkylene, $C_2$ to $C_5$ alkenylene or a phenylene group; |
| $X^5$ | = | a halogen atom, a methoxy or ethoxy group; |
| $Z^3$ | = | an acryl or methacryl group; |
| $k^2$ | = | 0 and 1; |
| $m^3$ | = | 0 and 1; |
| $k^2 + m^3$ | = | 0, 1 or 2. |

Such silanes are described for example in DE 34 07 087 A1.

Preferred zirconium, titanium compounds for the co-condensation with the named silanes are those according to formula (7)

$$MeX^6_yR^{23}_z \qquad \text{Formula (7)}$$

in which

| | |
|---|---|
| Me | stands for Zr or Ti; |
| $R^{23}$ | stands for a hydrogen atom, a substituted or unsubstituted $C_1$ to $C_{12}$ alkyl, $C_1$ to $C_{15}$ alkylaryl or $C_6$ to $C_{14}$ aryl group; |
| $X^6$ | stands for a halogen atom, a hydroxyl or $C_1$ to $C_8$ alkoxy group; |
| Y | is equal to 1 to 4; |
| z | is equal to 0 to 3. |

Preferred definitions, which can be selected independently of each other, for the individual variables are:

| | | |
|---|---|---|
| $R^{23}$ | = | a $C_1$ to $C_5$ alkyl or a phenyl group; |
| $X^6$ | = | a halogen atom, a methoxy, ethoxy or propoxy group; |
| y | = | 4; |
| z | = | 0 or 1, in particular 0. |

Particularly preferred zirconium and titanium compounds are $ZrCl_4$, $Zr(OC_2H_5)_4$, $Zr(OC_3H_7)_4$, $Zr(OC_4H_9)_4$, $ZrOCl_2$, $TiCl_4$, $Ti(OC_2H_5)_4$, $Ti(OC_3H_7)_4$ and $Ti(OC_4H_9)_4$.

Preferred aluminium compounds are those according to formula (8)

$$AlR^{24}_3 \qquad \text{Formula (8)}$$

in which

| | |
|---|---|
| $R^{24}$ | stands for a halogen atom, a hydroxyl or $C_1$ to $C_8$ alkoxy group, preferably for a halogen atom or a $C_1$ to $C_5$ alkoxy group. |

Particularly preferred aluminium compounds are $Al(OCH_3)_3$, $Al(OC_2H_5)_3$, $Al(OC_3H_7)_3$, $Al(OC_4H_9)_3$ and $AlCl_3$.

In addition, boron trihalides, tin tetrahalides, tln tetraalkoxides and/or vanadyl compounds are suitable for co-condensation with the above-named silanes.

The curing of the materials takes place, depending on the initiator used, by thermal, photochemical or redox-induced polymerization.

Peroxides, in particular dibenzoyl peroxide, dilauroyl peroxide, tert.-butyl peroctoate and tert.-butyl perbenzoate are preferred as initiators for the hot-curing systems. In addition, azobisisobutyroethylester, 2,2'-azobisisobutyronitrile (AIBN), benzopinacol and 2,2'-dialkylbenzopinacols are suitable.

Radical-supplying systems, for example benzoyl peroxide; lauroyl peroxide or preferably dibenzoyl peroxide, together with amines such as N,N-dimethyl-p-toluidine, N,N-dihydroxyethyl-p-toludine, N,N-dimethyl-sym.-xylidine or other structurally-related amines are used as initiators for cold polymerization. Amine and peroxide are usually distributed over two different components of the dental material. Upon mixing of the amine-containing base paste with the peroxide-containing initiator paste, the radical polymerization is initiated by the reaction of amine and peroxide.

Benzophenone and its derivatives as well as benzoin and its derivatives can be used for example as initiators for photopolymerization. Further preferred photoinitiators are the α-diketones such as 9,10-phenanthrenquinone, diacetyl, furil, anisil, 4,4'-dichlorobenzil and 4,4'-dialkoxybenzil. Camphorquinone and 2,2-methoxy-2-phenyl-acetophenone and in particular α-diketones in combination with amines as reduction agents are particularly preferably used. Preferred amines are 4-(N,N-dimethylamino)-benzoic acid ester, N,N-dimethylaminoethyl methacrylate, N,N-dimethyl- sym.-xylidine and triethanolamine. In addition, acyl phosphines such as e.g. 2,4,6-trimethylbenzoyldiphenyl- or bis-(2,6-dichlorobenzoyl)-4-N-propylphenylphosphinic oxide are also particularly suitable as photoinitiators.

For curing cationically polymerizable systems, diaryliodonium or triarylsulfonium salts such as e.g. triphenylsulfonium hexafluorophosphate or hexafluoro-antimonate are particularly suitable as well as the photoinitiator systems described in WO 96/13538 and WO 98/47047.

Furthermore, the mixtures can be filled with organic or inorganic particles or fibres to improve the mechanical properties. In particular, amorphous, spherical materials based on mixed oxides of $SiO_2$, $ZrO_2$ and/or $TiO_2$ with a mean average particle size of 0.005 to 2.0 μm, preferably from 0.1 to 1 μm, as disclosed for example in DE-PS 32 47 800, microfine fillers such as pyrogenic silicic acid or precipitation silicic acid as well as macro- or mini-fillers, such as quartz, glass ceramic or glass powder with an average particle size of 0.01 to 20 μm, preferably 0.5 to 5 μm as well as x-ray-opaque fillers such as ytterbium fluoride, are suitable as filler components. By mini-fillers are meant fillers with a particle size of 0.5 to 1.5 μm, and by macro-fillers fillers with a particle size of 10 to 20 μm.

Preferred compositions according to the invention contain, relative to their overall mass:
(a) 5 to 90% wt.-%, in particular 5 to 40 wt.-%, quite particularly preferably 10 to 20 wt.-% of one or more clusters according to formula (I),
(b) 10 to 90 wt.-%, in particular 10 to 80 wt.-% of one or more further polymerizable components,
(c) 0.1 to 5.0 wt.-%, in particular 0.2 to 2.0 polymerization initiator,
and
(d) 0 to 90 wt.-%, in particular 0 to 80 wt.-% filler.

The above composition can be further optimized in accordance with the desired use. Thus, a material which is particularly suitable as dental filling material preferably contains, in each case relative to the overall mass of the material:
(a) 5 to 20% wt.-% of one or more clusters according to formula (I),
(b) 0 to 20 wt.-% of one or more further polymerizable components,
(c) 0.2 to 2.0 wt.-% 2.0 polymerization initiator,
and
(d) 5 to 80 wt.-% filler.

A dental material which is particularly suitable as dental cement preferably contains, in each case relative to the overall mass of the material:
(a) 5 to 30% wt.-% of one or more clusters according to formula (I),
(b) 0 to 30 wt.-% of one or more further polymerizable components,
(c) 0.2 to 2.0 wt.-% 2.0 polymerization initiator, and
(d) 5 to 60 wt.-% filler.

A dental material which is particularly suitable as dental coating material preferably contains, in each case relative to the overall mass of the material:
(a) 5 to 40% wt.-% of one or more clusters according to formula (I),
(b) 5 to 80 wt.-% of one or more further polymerizable components,
(c) 0.2 to 2.0 wt.-% 2.0 polymerization initiator, and
(d) 0 to 40 wt.-% filler.

Quite particularly preferred are materials which contain, as further polymerizable component (b), 10 to 90 wt.-% polysiloxane and 0 to 40 wt.-% polymerizable organic monomers, in each case relative to the overall mass of the dental material.

These compositions are particularly suitable as dental materials, quite particularly as adhesives, for example for inlays, coating materials, cements and in particular filling materials. In general, the compositions are particularly suitable for those uses in which the curing of the material takes place in the mouth cavity.

After polymerization, the dental materials according to the invention have only a minimal content of unpolymerized constituents which can be dissolved out with aqueous or alcoholic solvents, which represents a significant improvement vis-à-vis conventional dental materials, as toxic side effects caused by monomeric constituents are suppressed.

According to the invention, clusters of a defined size and structure, i.e. pure, defined compounds of a known stoichiometry, are used for the preparation of dental materials, particularly preferably clusters with monodispersed mass distribution. In this way, the material properties of the dental materials, such as for example E-modulus, strength, hardness and abrasivity, can be set and improved in a controlled manner. Dental materials which contain 1 to 2 different clusters are preferred.

In the following, the Invention is explained in more detail using examples.

EXAMPLE 1

Synthesis of the Oxozirconium Methacrylate Cluster of Composition $Zr_4O_2(OMc)_{12}$ 2.04 g (24 mmol) methacrylic acid were added to 1.73 g (3.6 mmol) of an 80% solution of zirconium butylate (Zr $(OC_4H_9)_4$) in n-butanol. The reaction mixture was left to stand for a day at room temperature and the formed precipitate filtered off accompanied by the exclusion of moisture. 1.09 g (86% yield) of colourless cubic crystals resulted, which are soluble in chloroform, ethanol or toluene.

EXAMPLE 2

Synthesis of Matrix Substances Based on Silicic Acid Polycondensate

A) Hydrolytic Condensation of bis[(methacryloyloxy) propoxycarbonylethyl)-[3-(triethoxysilylpropyl)]amine:

16.1 g (26 mmol) bis [(methacryloyloxy)propoxy-carbonylethyl) -[3-(triethoxysilylpropyl)] amine which is obtainable by Michael addition of 3-aminopropyltriethoxysilane to 2-(acryloyloxyethyl)-propyl methacrylate (cf. EP 1 022 012) were dissolved in 37.5 ml anhydrous ethanol and hydrolytically condensed accompanied by the addition of 2.81 g of an aqueous 0.1 N ammonium fluoride solution. After 24 h stirring at room temperature, the volatile components were removed in vacuum and approx. 12 g of a relatively low-viscosity resin (SG-1) with a viscosity of c=ca. 8 Pas (23° C.) remained. This and all other viscosity data, unless otherwise stated, involves the rotation viscosity measured with a rotation rheometer with a parallel-plate measuring system, CV=120 (model CVO 120 of the company Bohlin).

B) Hydrolytic condensation of (3-triethoxysilyl-propy-laminocarbonyl) butyric acid-(1,3(2)-bismethacryl-oyloxypropyl)ester:

10.9 g (20 mmol) (3-triethoxysilylpropylamido)butyric acid-(1,3-(2)-bismethacryloyloxypropyl)ester, which was obtained by amidation from 3-aminopropyltriethoxysilane with the adduct from glycerin dimethacrylate and glutaric acid anhydride (cf. EP 1 022 012), were dissolved in 98.2 mol anhydrous ethyl acetate and hydrolytically condensed accompanied by the addition of 1.08 g 0.5 N hydrochloric acid. After 30 minutes' stirring at 40° C., the volatile components were removed in vacuum. The resin obtained was then sylilated after dissolving in a mixture of 35 g tert.-butlmethyl-ether, 12 g THF and 1.45 g (12 mmol)

2,4,6-trimethylpyridine by the dropwise addition of 1.96 g (18 mmol) trimethylchlorosilane. After stirring overnight at room temperature, the reaction mixture was washed with diluted hydrochloric acid and saturated NaCl solution and then dried over anhydrous sodium sulphate. After the evaporation of the solvent in vacuum, ca. 6 g of a viscous resin (SG-2) with a viscosity of η=ca. 75 Pas (23° C.) remained.

EXAMPLE 3

Preparation of Dental Materials Based on Clusters According to Example 1

Various materials were prepared starting from the cluster $Zr_4O_2(OMc)_{12}$ from example 1 and the matrix substances ST-1 and SG-2. The clusters were mixed with the matrix substances as 10% solution in ethanol and the solvent evaporated off in vacuum after the addition of the initiator components. The compositions (mass %) of the thus-prepared unfilled materials M-1 to M-5 are listed in Table 1. To determine the mechanical properties, testpieces with the dimensions 25×2×2 mm were prepared from the compositions and cured by illumination with light of a wavelength of 390 to 500 nm (6 minutes). For this purpose, a dental radiation source of the Spectramat type from Vivadent was used. The bending strength (BS) and the bending E-modulus (BEM) were determined according to the ISO standard 4049 (2000), the testpieces having been previously stored in water at 37° C. for 24 h. In addition, BS and BEM values were also measured for samples which were stored dry for 24 h at 37° C.

TABLE 1

Composition (mass %) of the unfilled materials M-1 to M-5

|  | M-1*) | M-2 | M-3*) | M-4 | M-5 |
|---|---|---|---|---|---|
| SG-1 | 98.7 | 86.7 | — | — | — |
| SG-2 | — | — | 98.7 | 88.7 | 78.7 |
| Zr-Cluster from Example 1 | — | 10.0 | — | 10.0 | 20 |
| Photoinitiator[a]) | 1.3 | 1.3 | 1.3 | 1.3 | 1.3 |

*) Comparison example without clusters
a) A mixture of 0.3% camphorquinone, 0.6% 4-(N,N-dimethylamino)-benzoic acid ethyl ester and 0.4% acryl phosphinic oxide (Lucerin TPO, BASF) was used as photoinitiator

TABLE 2

Bending strength (BS) and Bending E-modulus (BEM) of materials M-1 to M-5

|  | M-1*) | M-2 | M-3*) | M-4 | M-5 |
|---|---|---|---|---|---|
| Dry BF (MPa) | 46 | 47 | 48 | 59 | 70 |
| H₂O storage BS (MPa) | 31 | 52 | 36 | 60 | 60 |
| Dry BEN (MPa) | 1230 | 1900 | 1820 | 2100 | 2400 |
| H₂O storage BEM (MPa) | 1000 | 1920 | 1750 | 2270 | 2600 |

*) Comparison example without clusters

To prepare the composite pastes C-1 to C-5, the unfilled materials M-1 to M-5 were mixed with the quantities of filler given in Table 3. Silanized pyrogenic silicic acid with an average primary particle size of 40 nm and a BET surface of 50 m²/g (silanized Aerosil OX-50, Degussa), ytterbium trifluoride with an average particle size of 5 μm and a BET surface of <7.5 m²/g (YbF₃, Auer Remy), silanized $SiO_2$— $ZrO_2$ mixed oxide with a primary particle size of 130 to 230 nm (Sphärosil, Tokoyma Soda) and silanized barium silicate glass (Ba—Si glass) with an average particle size of 1.2 μm were used as fillers. The filler components are incorporated by means of a capsule vibrator.

The bending strength and the bending E-modulus were then measured, in each case after 24-hour storage in water or in the dry. The results are summarized in Table 4.

TABLE 3

Composition of the composite pastes C-1 to C-5 (values in mass %)

|  | (K-1*) | K-2 | K-3*) | K-4 | K-5 |
|---|---|---|---|---|---|
| Unfilled material | 25.0 (M-1) | 25.0 (M-2) | 25.0 (M-3) | 25.0 (M-4) | 25.0 (M-5) |
| Aerosil OX-50 | 1.0 | 1.0 | 1.0 | 1.0 | 1.0 |
| YbF₃ | 15.0 | 15.0 | 15.0 | 15.0 | 15.0 |
| Spharosil | 15.0 | 15.0 | 15.0 | 15.0 | 15.0 |
| Ba-Si glass | 44.0 | 44.0 | 44.0 | 44.0 | 44.0 |

*) Comparison example without clusters

TABLE 4

Bending strength (BS) and bending E-modulus (BEM) of the composites C-1 to C-5

|  | (K-1*) | K-2 | K-3*) | K-4 | K-5 |
|---|---|---|---|---|---|
| Dry BS (MPa) | 94 | 96 | 89 | 101 | 103 |
| H₂O storage BS (MPa) | 68 | 100 | 89 | 110 | 113 |
| Dry BEM (MPa) | 6400 | 8900 | 8150 | 9100 | 9840 |
| H₂O storage BEM (MPa) | 5500 | 9300 | 7160 | 9750 | 10900 |

*) Comparison without clusters

The results show (Tables 2 and 4) that the addition of clusters of the composition $Zr_4O_2(OMc)_{12}$ in each case leads to an improvement in strength and to an increase in E-modulus of the materials. In addition, in the case of the cluster-containing materials, an increase in the E-modulus after water storage can be observed, whereas the E-modulus decreases in the case of the non-modified samples M-1/C-1 and M-3/C-3 after water storage.

Samples of the cured composites C-2 and C-4 were crushed and the fragments dispersed in ethanol at 37° C. After 72 h, the solid constituents were filtered off and the filtrate concentrated to dryness. Almost no residue resulted, which indicates a complete incorporation of the polymerizable components into the polymer network of the composite matrix.

The invention claimed is:

1. Dental material containing a cluster according to the general formula $$[(M^1)_a(M^2)_bO_c(OH)_d(OR)_e(L\text{-Sp-Z})_f]  \quad (I)$$

in which

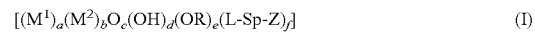

| $M^1, M^2$ | independently of each other, stand for a metal atom of the IIIrd or Vth main groups or the Ist to VIIIth sub-groups of the periodic table; |
| R | is an alkyl group with 1 to 6 carbon atoms; |
| L | is a co-ordinating group with 2 to 6 complexing centres; |
| Sp | is a spacer group or is absent; |
| Z | is a polymerizable group; |

-continued

| | |
|---|---|
| a | is a number from 1 to 20; |
| b | is a number from 0 to 10; |
| c | is a number from 1 to 30; |
| d, e | independently of each other, are in each case a number from 0 to 30; |
| f | is a number from 2 to 30, | any charge of the cluster (I) present being neutralized by counterions, one or more further polymerizable components, and at least one filler.

2. Dental material according to claim 1, characterized in that the variables have the following meanings:

| | |
|---|---|
| $M^1$, $M^2$ | = independently of each other, Ti and/or Zr; |
| R | = an alkyl group with 1 to 4 carbon atoms, in particular 1 to 2 carbon atoms; |
| L | = α-hydroxycarboxylate (—CH(OH)—COO$^-$), α-aminocarboxylate (—CH(NH$_2$)—COO$^-$), β-diketonate ([—C(—O$^-$)=CH—C(=O)R$^K$] with R$^K$ = alkyl; methyl, sulfonate (—SO$_3^-$), phosphonate (—PO$_3^{2-}$), or carboxylate (—COO$^-$); |
| Sp | = an alkylene group with 1 to 18 arbon atoms, an oxyalkylene group with 1 to 18 carbon atoms and 0 to 6 oxygen atoms or an arylene group with 6 to 14 carbon atoms, the spacer Sp being able to contain one or more, preferably 0 to 2 of the groups O, S, CO—O, O—CO, CO—NH, NH—CO, O—CO—NH, NH—CO—O and NH; particularly preferably, Sp is an alkylene group with 1 to 6, in particular 1 to 3 carbon atoms or is absent; |
| Z | = an ethylenically unsaturated group, an epoxide, oxetane, vinyl ether, 1,3-dioxolane, spiroorthoester, |

-continued

| | |
|---|---|
| | particularly preferably a methacrylic and/or acrylic group; |
| a | = 2 to 11; |
| b | = 0 to 4. |

3. Dental material according to claim 2, characterized in that L-Sp-Z stands for acrylate, methacrylate, oleate, allyl acetoacetate and/or acetoacetoxyethyl methacrylate.

4. Dental material according to claim 2, characterized in that the clusters contain 1 to 4 kinds of ligands of the type L-Sp-Z.

5. Dental material according to claim 2, characterized in that the cluster has a monodisperse mass distribution.

6. Dental material according to claim 2, characterized in that the indices c to f assume values such that the positive charges of the metal or metals are completely neutralized.

7. Dental material according to claim 2, characterized in that $M^1$ is equal to $M^2$.

8. Dental material according to claim 2, characterized in that the further polymerizable component is a polymerizable polysiloxane, an ionically and/or radically polymerizable organic monomer or a mixture thereof.

9. Dental material according to claim 2, characterized in that it contains an initiator for ionic andlor radical polymerization, and/or further additives.

10. Dental material according to claim 1, characterized in that it contains, relative to its overall mass
    (a) 5 to 90 wt.-% of at least one cluster according to formula (I),
    (b) 10 to 90 wt.-% of a further polymerizable component,
    (c) 0.1 to 5.0 wt.-% polymerization initiator, and
    (d) 0 to 90 wt.-% filler.

11. Dental material according to claim 2, characterized in that $R^k$=$C_1$ to $C_6$ alkyl.

* * * * *